(12) United States Patent
Terrill-Grisoni et al.

(10) Patent No.: US 6,270,529 B1
(45) Date of Patent: Aug. 7, 2001

(54) MODULAR IMPLANT FOR REPLACING END OF RADIUS AND HAVING DRAINAGE PASSAGE FOR TRAPPED FLUID

(75) Inventors: Lauralan Terrill-Grisoni, Cordova; Nathaniel Kelley Grusin, Memphis; Donald E. Raynor, Burlison; Maureen Theis-Handwerker, Germantown, all of TN (US); Stuart D. Patterson, Winter Haven, FL (US); Graham J. W. King; James A. Johnson, both of London (CA)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 09/388,093

(22) Filed: Sep. 1, 1999

(51) Int. Cl.[7] ........................................................ A61F 2/38
(52) U.S. Cl. ..................................... 623/20.11; 623/18.11
(58) Field of Search ............................. 623/20.11, 20.12, 623/20.13, 23.39, 23.42, 18.11, 16.11, 11.11, 116

(56) References Cited

U.S. PATENT DOCUMENTS

| | | | |
|---|---|---|---|
| 3,739,403 | * | 6/1973 | Nicolle . |
| 4,242,758 | | 1/1981 | Amis et al. . |
| 5,030,237 | | 7/1991 | Sorbie et al. ........................... 623/20 |
| 5,728,161 | * | 3/1998 | Camino et al. . |
| 5,769,093 | * | 6/1998 | Bays . |
| 5,782,922 | | 7/1998 | Vandewalle ............................. 623/20 |
| 5,879,395 | | 3/1999 | Tornier et al. .......................... 623/20 |
| 5,885,297 | | 3/1999 | Matsen, III ............................. 606/87 |

OTHER PUBLICATIONS

"The Sorbie–Questor® Total Elbow System", ©1996, Wright Medical Technology, Inc.
"Swanson Titanium Radial Head Implant, regular and narrow stem" © 1995, Wright Medical Technology, Inc.

* cited by examiner

Primary Examiner—Jeffrey A. Smith
(74) Attorney, Agent, or Firm—Walker, McKenzie & Walker, P.C.

(57) ABSTRACT

A system including modular radial head implants, sizers for trial reduction of the joint, and instrumentation for preparing the radial head, implanting the sizers, assembling the implants.

4 Claims, 9 Drawing Sheets

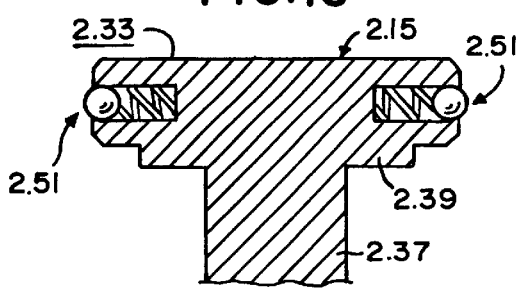
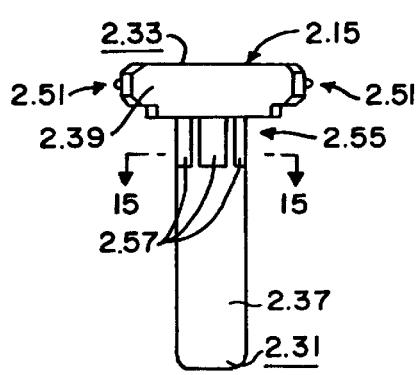
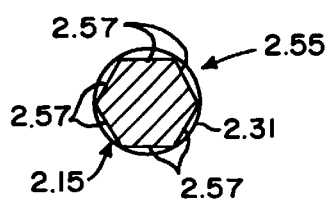
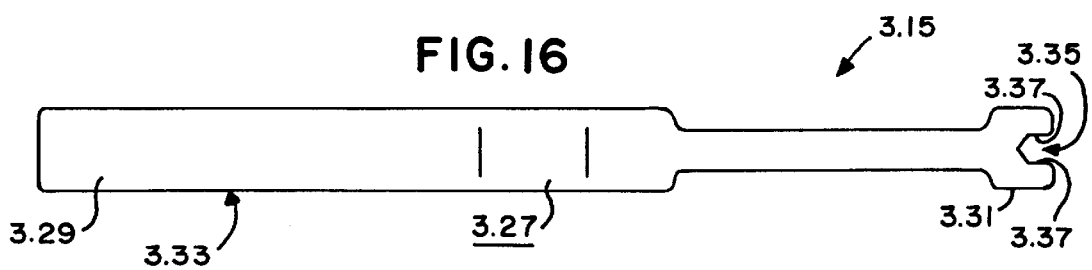
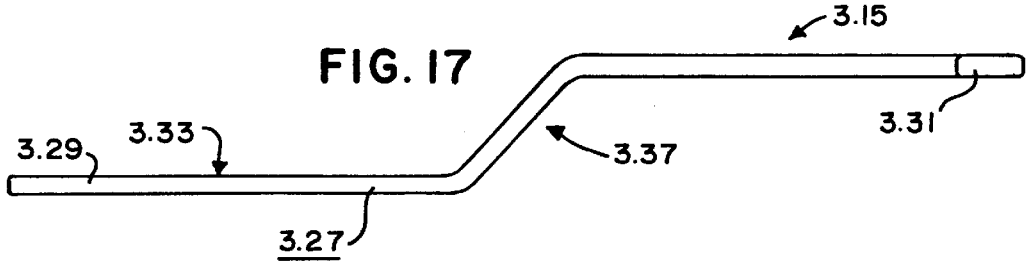
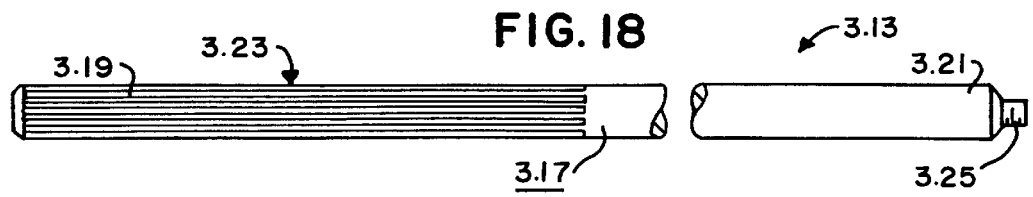

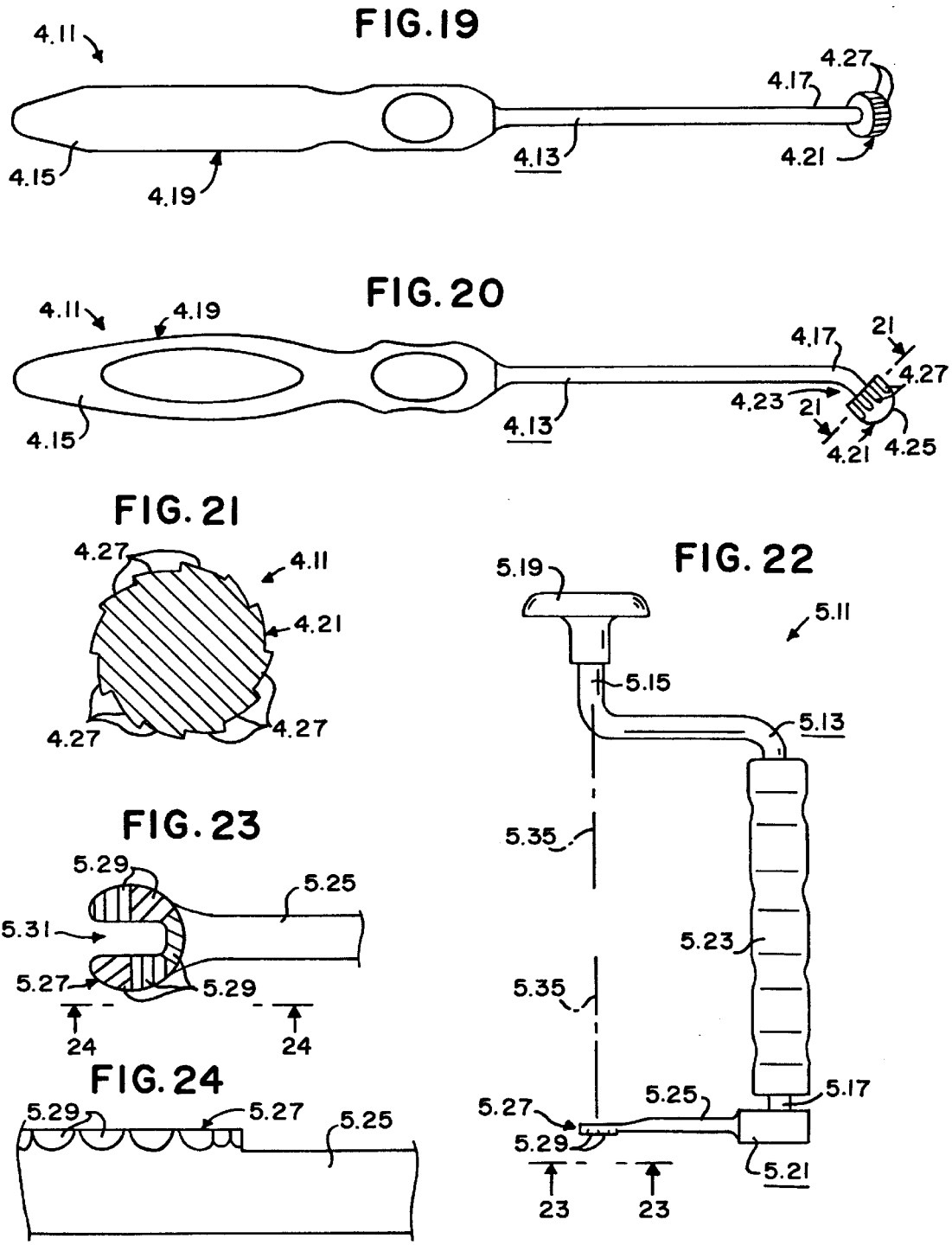

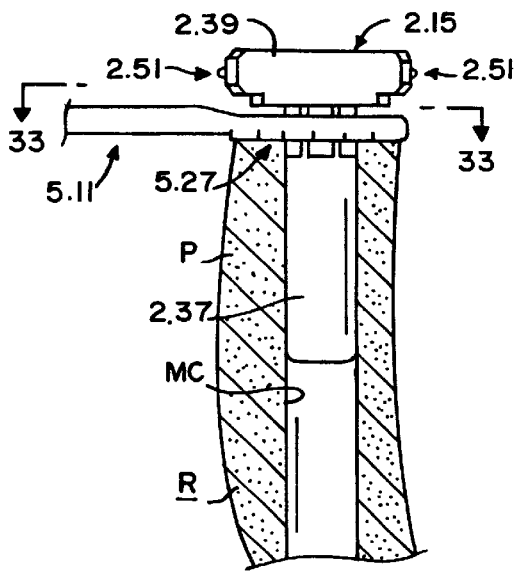
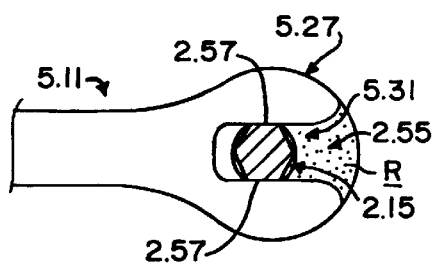
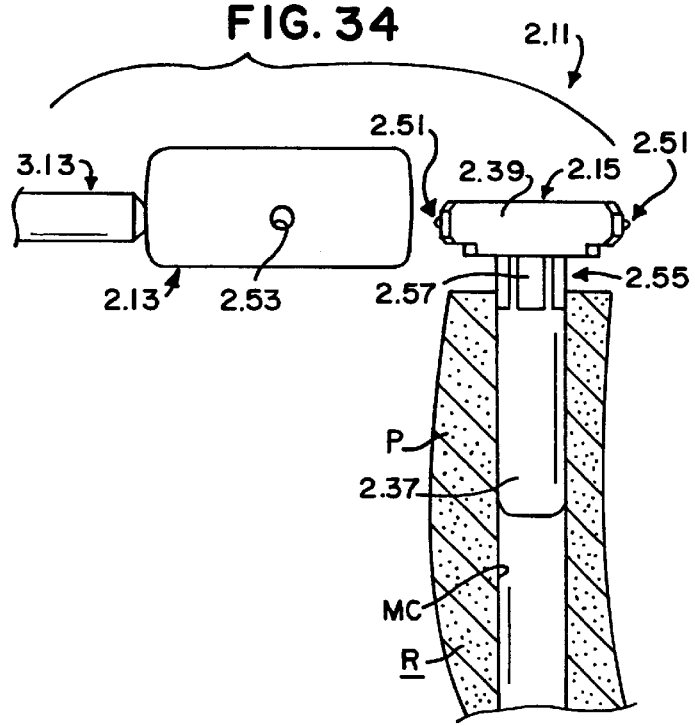
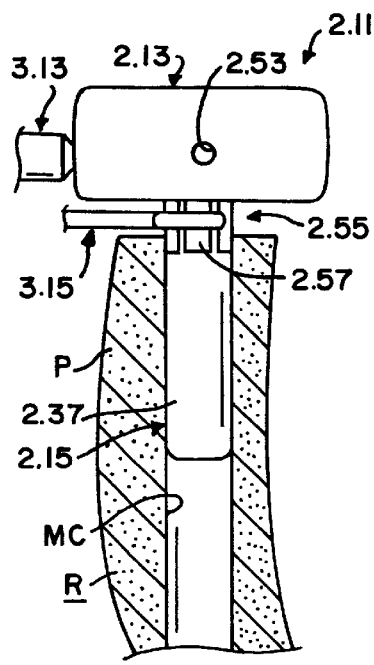

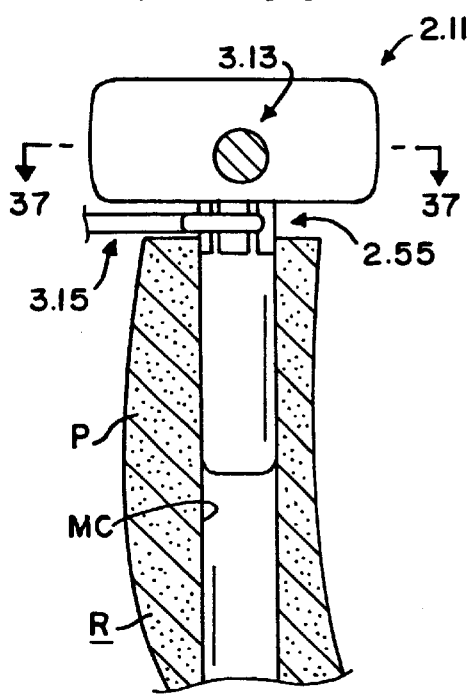
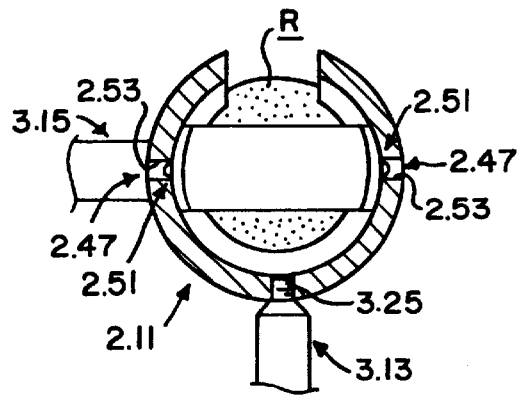
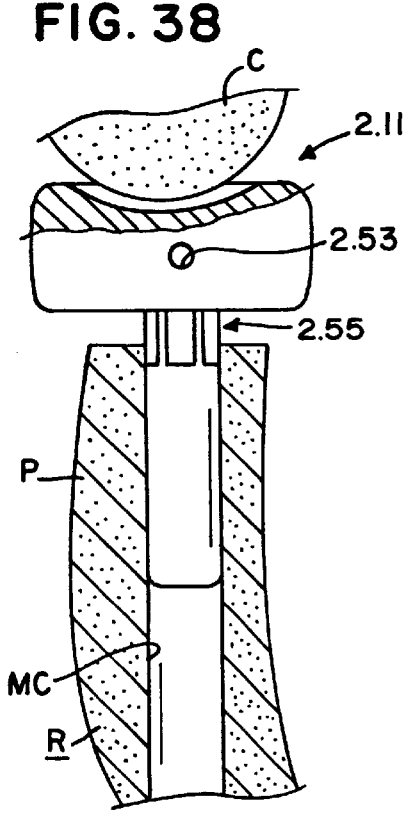
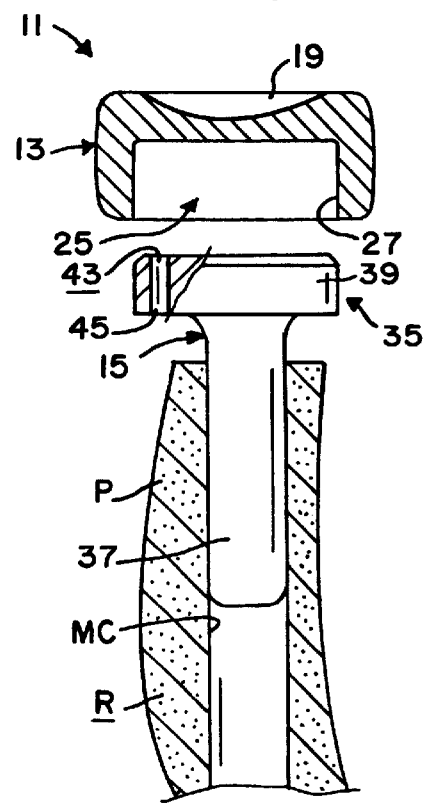

MODULAR IMPLANT FOR REPLACING END OF RADIUS AND HAVING DRAINAGE PASSAGE FOR TRAPPED FLUID

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates generally to implantable orthopaedic prostheses and more particularly to a system including modular radial head implants, sizers for trial reduction of the joint, and instrumentation for preparing the radial head, implanting the sizers, assembling the implants, etc.

2. Information Disclosure Statement

Prostheses for replacing or repairing the radial head are well known in the prior art. The Sorbie-Questor® Total Elbow System includes a radial head component having a metal base and a polyethylene articulating surface cap molded onto the metal base. The Swanson Titanium Radial Head Implant is a one-piece implant manufactured from commercially pure titanium that features nitrogen ion implantation for increased surface hardness, and is provided in five different sizes to meet various operative requirements.

BRIEF SUMMARY OF THE INVENTION

The present invention provides a modular implant for replacing the head of the proximal end of a radius and for articulating with the capitellum of a humerus. The implant of the present invention comprises, in general, a modular head including a proximal end having a concavity therein for articulating with the capitellum of the humerus, and including a first lock member; and a modular body including distal end for connecting to the radius, including a second lock member for coacting with the first lock member of the modular head to lock the modular head and the modular body together, and having a drainage passage allowing fluid trapped between the first and second lock members to drain out.

BRIEF DESCRIPTION OF THE SEVERAL VIEWS OF THE DRAWINGS

FIG. 13 is a sectional view substantially as taken on line 13—13 of FIG. 12, on a somewhat enlarged scale.

FIG. 14 is a side elevational view of the modular body of FIG. 12.

FIG. 15 is a sectional view substantially as taken on line 15—15 of FIG. 14.

FIG. 16 is a top plan view of a preferred embodiment of a modular body sizer insertion instrument of the present invention.

FIG. 17 is a side elevational view of the modular body sizer insertion instrument of FIG. 16.

FIG. 18 is a plan view of a preferred embodiment of a modular head sizer insertion instrument of the present invention.

FIG. 19 is a top plan view of a preferred embodiment of a modular radial head broach of the present invention.

FIG. 20 is a side elevational view of the modular radial head broach of FIG. 19.

FIG. 21 is a sectional view substantially as taken on line 21—21 of FIG. 20, on a somewhat enlarged scale.

FIG. 22 is an elevational view of a preferred embodiment of a modular radial head radius crank planer of the present invention, with portions thereof broken away to shown internal structure.

FIG. 23 is a plan view of a portion of the radius crank planer substantially as taken on line 23—23 of FIG. 22, on a somewhat enlarged scale.

FIG. 24 is an elevational view of a portion of the radius crank planer substantially as taken on line 24—24 of FIG. 23, on a somewhat enlarged scale.

FIG. 32 is a sectional view similar to FIG. 31, but showing the planer portion of the modular radial head radius crank planer fully positioned on the stem of the modular body of the modular radial head sizer.

FIG. 33 is a sectional view substantially as taken on line 33—33 of FIG. 32.

FIG. 34 is a sectional view similar to FIG. 32, but showing the modular radial head radius crank planer removed from the stem, and showing the modular head of the modular radial head sizer screwed onto the modular sizer head insertion tool and being slipped onto the boss of the modular body of the modular radial head sizer.

FIG. 35 is a sectional view similar to FIG. 34, but showing the modular head fully inserted onto the boss, and showing modular head sizer insertion instrument of the present invention engaging the flats of the neck portion of the stem of the modular body of the modular radial head sizer.

FIG. 36 is a sectional view similar to FIG. 35, but showing the modular body sizer insertion instrument and modular head sizer insertion instrument fully mounted on the respective modular body and modular head, and showing the modular body and modular head rotated 90° with respect to one another and locked together.

FIG. 37 is a sectional view substantially as taken on line 37—37 of FIG. 35.

FIG. 38 is a sectional view similar to FIG. 36, but showing the modular body sizer insertion instrument and modular head sizer insertion instrument removed therefrom, and illustrating a trial reduction of the proximal end of the radius and the capitellum of the humerus.

FIG. 39 is a sectional view similar to FIG. 38, but showing the modular radial head sizer removed from the radius, showing the stem of the modular body of the modular radial head implant of the present invention being placed into the medullary canal of the radius, and showing the modular head of the modular radial head implant being placed onto the boss of the modular body thereof.

DETAILED DESCRIPTION OF THE INVENTION

The preferred embodiment of the system of the present invention is used for replacing or resurfacing the radial head of an elbow joint. However, it should be understood that the system of the present invention could be used for other joints, with modifications to accommodate the particular size and anatomical shape and positioning, etc., without changing the essential structure and operation of the system of the present invention.

Figure 28:
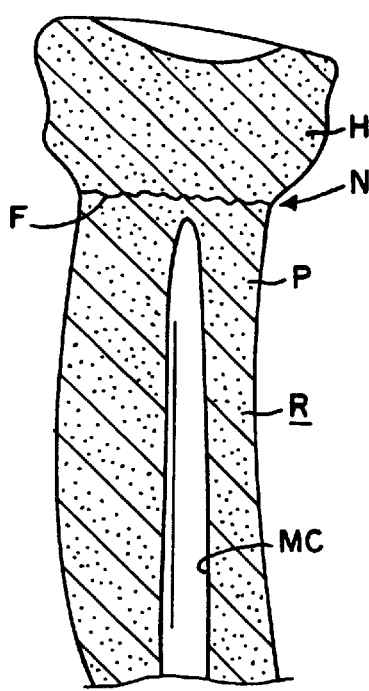
FIG. 28 is a sectional view of the proximal end of a radius, having a fractured neck.
Figure 29:
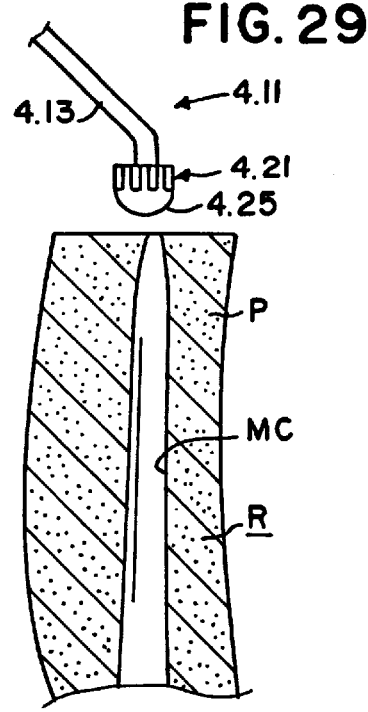
FIG. 29 is a sectional view similar to FIG. 28, but with the head and a portion of the neck of the proximal end of the radius excised, and showing the head of a modular radial head broach of the present invention being used to prepare the medullary canal of the proximal end of the radius.
Figure 30:
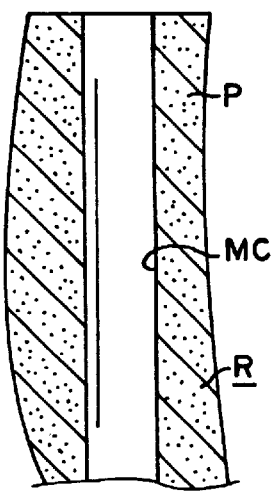
FIG. 30 is a sectional view similar to FIG. 29, but showing the medullary canal of the proximal end of the radius prepared for implantation.
Figure 31:
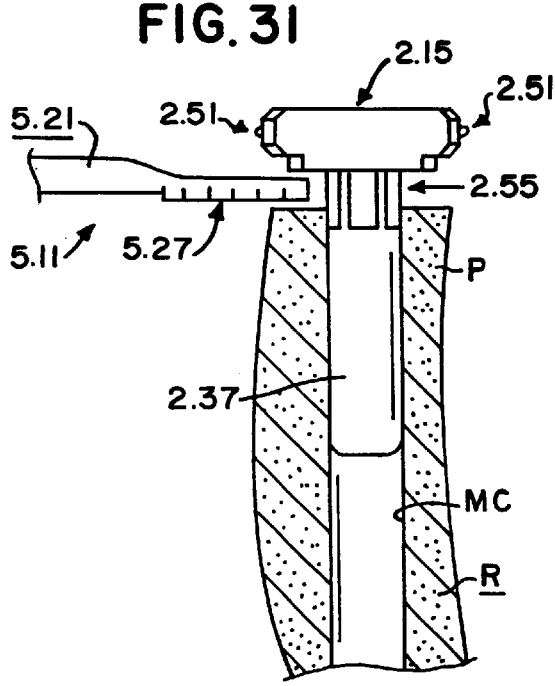
FIG. 31 is a sectional view similar to FIG. 30, but showing the stem of the modular body of the modular radial head sizer of the present invention inserted into the medullary canal, and showing the planer portion of the modular radial head radius crank planer of the present invention being slipped onto the stem.
Figure 40:
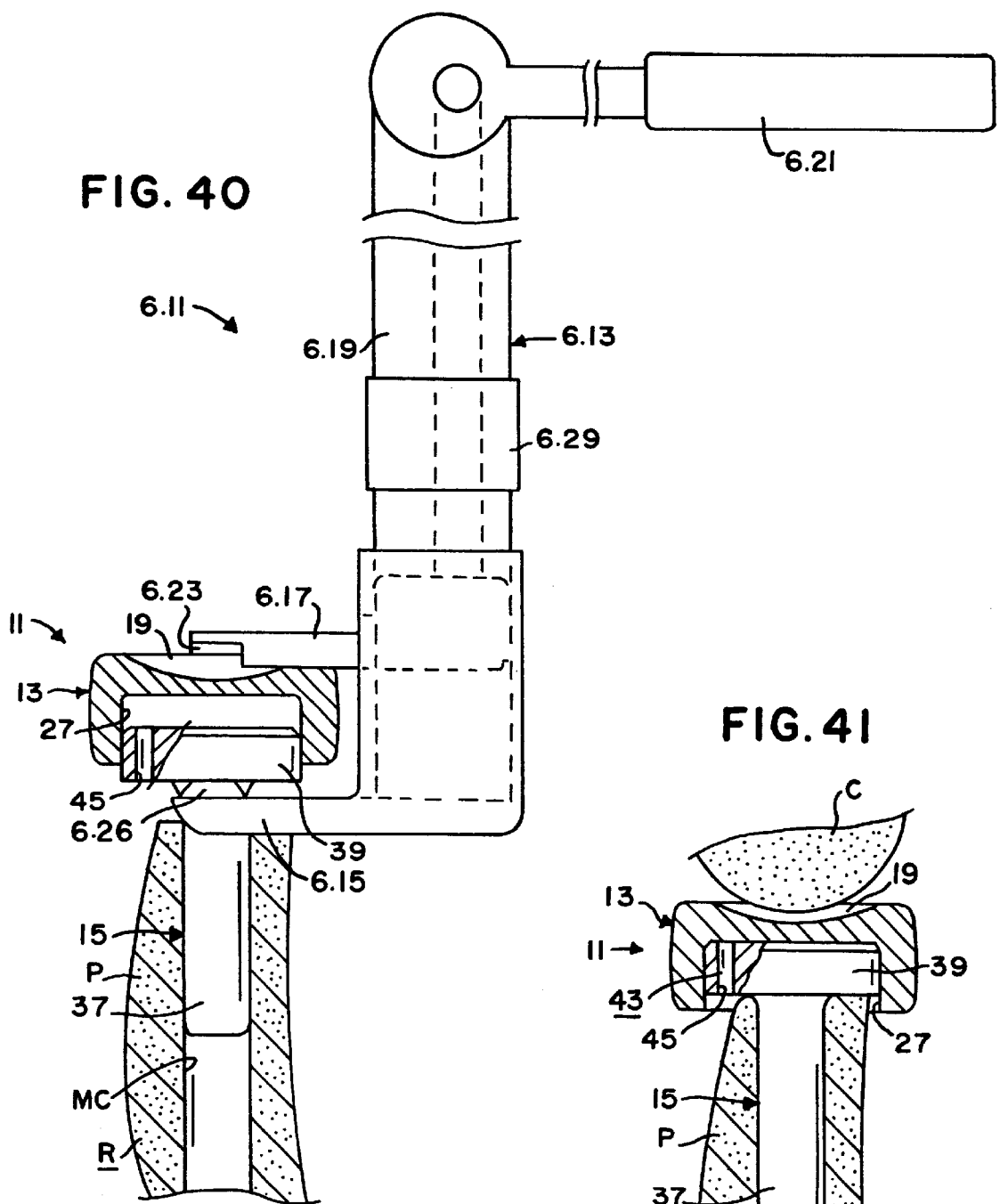
FIG. 40 is a sectional view similar to FIG. 39 but showing the modular radial head locking instrument of the present invention engaging the modular radial head implant to lock the modular head and modular body thereof together.

The system of the present invention includes a modular radial head implant 11 (see, in general, FIGS. 39–41) for replacing the head H of the proximal end P of a radius R in the event the neck N of the proximal end P of the radius R has a fracture F (see, in general, FIG. 28), or the head H otherwise needs to be replaced. The modular radial head implant 11 includes a modular head 13 (see, in general, FIGS. 1–4) and a modular body 15 (see, in general, FIGS. 5 and 6).

Figure 41:
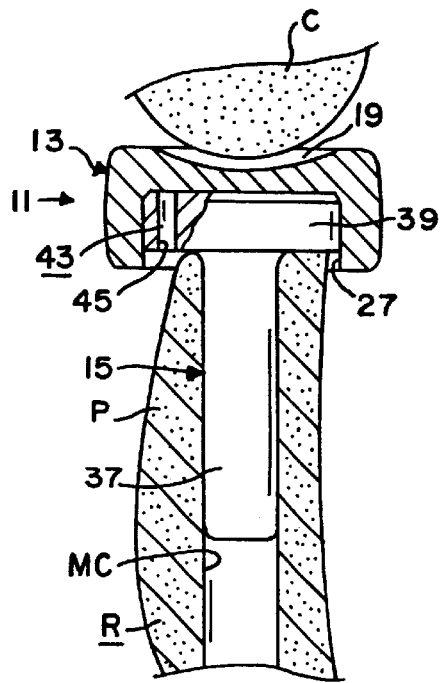
FIG. 41 is a sectional view similar to FIG. 40, but with the modular radial head locking instrument removed, with the modular head and modular body locked together, and illustrating a reduction of the proximal end of the radius and the capitellum of the humerus.

The modular bead 13 includes a proximal end 17 having a slight concavity 19 therein for articulation with the capitellum C of a humerus (see FIG. 41). The modular head 13 has a distal end 21 and an outer wall 23 extending between the proximal and distal ends 17, 21 thereof. The outer wall 23 of the modular head 13 preferably curves outwardly slightly between said proximal and distal ends 17, 21 thereof as clearly shown in FIGS. 2 and 3 with the modular head 13 forming a circular disc with a barrel-shaped outer wall. The modular head 13 thus substantially reproduces the anatomical articular geometry of the head H, or proximal end P, of a radius R. The modular head 13 includes a first lock member 25. The first lock member 25 preferably has a cavity 27 with a female taper. For example, the sides of the cavity 27 preferably taper inwardly from the distal end 21 of the modular head 13 a combined total of approximately 3° as indicated by the arrow 29 in FIG. 2.

Figure 1:
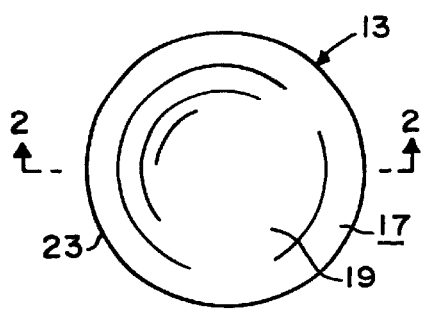
FIG. 1 is a top plan view of a modular head of the preferred embodiment of a modular radial head implant of the present invention.
Figure 2:
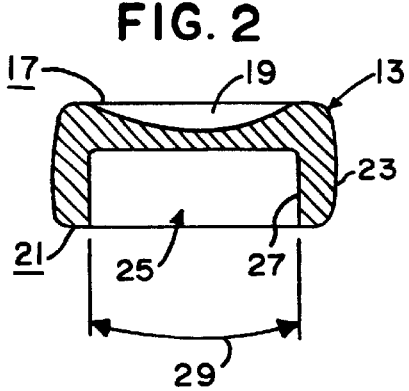
FIG. 2 is a sectional view substantially as taken on line 2—2 of FIG. 1.
Figure 3:
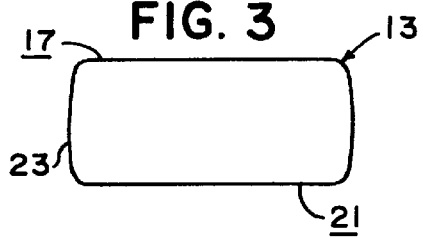
FIG. 3 is side elevational view of the modular head of FIG. 1.
Figure 4:
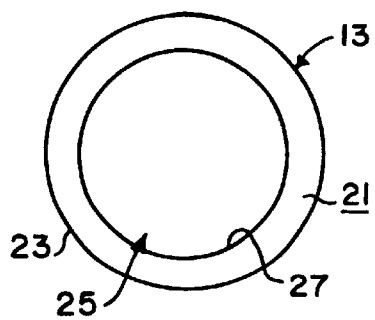
FIG. 4 is bottom plan view of the modular head of FIG. 1.
Figure 5:
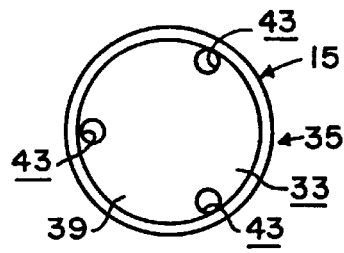
FIG. 5 is a top plan view of a modular body of the preferred embodiment of a modular radial head implant of the present invention.
Figure 6:
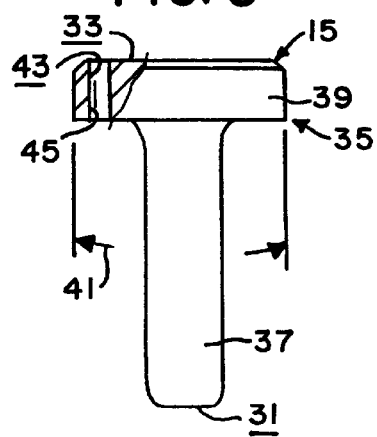
FIG. 6 is a side elevational view of the modular body of FIG. 5.
Figure 7:
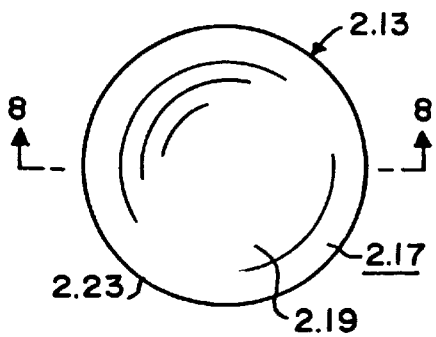
FIG. 7 is a top plan view of a modular head of the preferred embodiment of a modular radial head sizer of the present invention.
Figure 8:
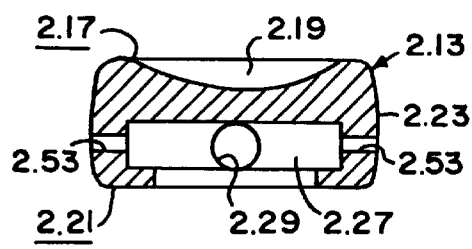
FIG. 8 is a sectional view substantially as taken on line 8—8 of FIG. 7.

The modular body 15 includes a distal end 31 for engaging the proximal end P of the radius R (see FIGS. 39–41), and a proximal end 33. The modular body 15 includes a second lock member 35 for coacting with the first lock member 25 of the modular head 13 to lock the modular head 13 and the modular body 15 together. The distal end 31 of the modular body 15 preferably has a elongated stem 37 for extending into the medullary canal MC of the proximal end P of the radius R (see FIGS. 39–41). The proximal end 33 of the modular body 15 preferably has an enlarged boss or platform 39 for fitting into the cavity 27 of the first lock member 25 of the modular head 13. The platform 39 preferably has a male taper for coacting with the female taper of the cavity 27 of the first lock member 25 of the modular head 13 to lock the modular head 13 and the modular body 15 together. For example, the sides of the platform 39 preferably taper outwardly from the proximal end 33 of the modular body 15 a combined total of approximately 3° as indicated by the arrow 41 in FIG. 6, and the platform 39 is preferably sized so as to tightly fit into the cavity 27 so that the male and female tapers will securely lock together when the modular head 13 and modular body 15 are forcibly brought together as will now be apparent to those skilled in the art. The modular body 15 has a drainage passage 43 allowing fluid trapped between the first and second lock members 25, 33 to drain out. The drainage passage 43 preferably consists of a hole or aperture 45 extending through the platform 39 from the proximal end 33 of the modular body 15, through the platform 39 to a point exterior of the stem 37 as clearly shown in FIG. 6. Preferably, the modular body 15 has a plurality of spaced drainage passages 43 through the platform 39 as shown in FIG. 5.

The modular head 13 and modular body 15 may be constructed in various manners and out of various materials as will now be apparent to those skilled in the art to substantially reproduce anatomical articular geometry. Thus, for example, the modular head 13 and modular body 15 can each be machined or otherwise constructed as a one-piece, integral unit out of a medical grade, physiologically acceptable material such as a cobalt chromium molybdenum alloy or the like, in various sizes to fit a range of typical patients, etc. The modular head 13 and modular body 15 are preferably highly polished. Preferably, the modular radial head implant 11 includes a plurality of different size modular heads 13 and bodies 15 for allowing different size modular radial head implants 11 to be assembled from individual heads 13 and bodies 15. Thus, for example, modular heads 13 may be provided with 5 different head diameters ranging between 20 and 28 millimeters in 2 millimeter increments, and with 3 different head heights ranging between 9 and 13 millimeters in 2 millimeter increments. Modular bodies 15 may be provided with 5 different stem diameters ranging between 5.5 and 9.5 millimeters in 1 millimeter increments, and with 3 different stem lengths ranging between 20 and 24 millimeters in 2 millimeter increments. The various heads 13 and bodies 15 are preferably universally modular, so that all of the bodies 15 will work with all of the heads 13, and vice versa.

The system of the present invention includes a modular radial head sizer 2.11 (see, in general, FIGS. 34–38) for allowing a trial reduction of the elbow joint to help determine the proper size modular radial head implant 11 to use as will now be apparent to those skilled in the art. The modular radial head sizer 2.11 includes a modular head 2.13 (see, in general, FIGS. 7–11) and a modular body 2.15 (see, in general, FIGS. 12–15).

Figure 9:
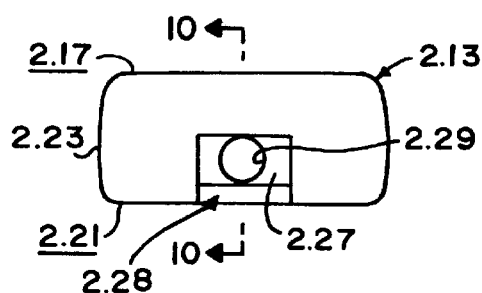
FIG. 9 is side elevational view of the modular head of FIG. 7.
Figure 10:
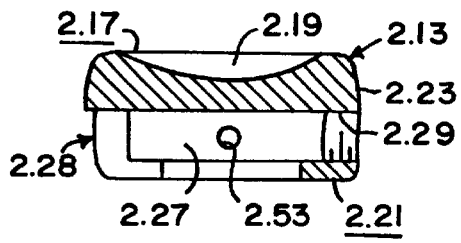
FIG. 10 is a sectional view substantially as taken on line 10—10 of FIG. 9.
Figure 11:
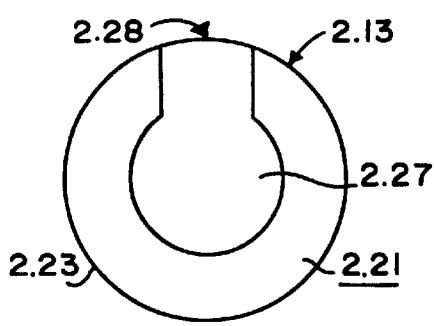
FIG. 11 is bottom plan view of the modular head of FIG. 7.
Figure 12:
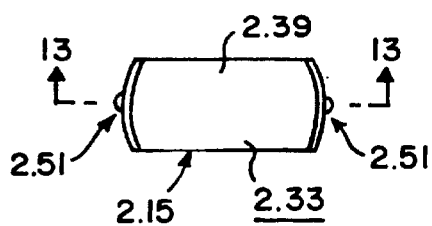
FIG. 12 is a top plan view of a modular body of the preferred embodiment of a modular radial head sizer of the present invention.

The modular head 2.13 includes a proximal end 2.17 having a slight concavity 2.19 therein for articulation with the capitellum C of a humerus (see FIG. 38) during trial reduction of the modular radial head sizer 2.11. The modular head 2.13 has a distal end 2.21 and an outer wall 2.23 extending between the proximal and distal ends 2.17, 2.21 thereof. The outer wall 2.23 of the modular head 2.13 preferably curves outwardly slightly between said proximal and distal ends 2.17, 2.21 thereof as clearly shown in FIGS. 8–10 with the modular head 2.13 forming a circular disc with a barrel-shaped outer wall. The modular head 2.13 thus substantially reproduces the anatomical articular geometry of the head H, or proximal end P, of a radius R. The modular head 2.13 has a cavity 2.27 for lockably receiving a portion of the modular body 2.15 as will hereinafter become apparent, and has a side entrance opening 2.28 to the cavity 2.27 through the outer wall 2.23. The modular head 2.13 preferably has a internally threaded aperture or cavity 2.29 extending into or through the outer wall 2.23. As indicated in FIGS. 9 and 10, the threaded cavity 2.29 may be directly opposite the side entrance opening 2.28.

The modular body 2.15 includes a distal end 2.31 for engaging the proximal end P of the radius R (see, in general, FIGS. 31, 32, 34–36 and 38), and a proximal end 2.33. The distal end 2.31 of the modular body 2.15 preferably has a elongated stem 2.37 for extending into the medullary canal MC of the proximal end P of the radius R (see FIGS. 31, 32, 34–36 and 38). The proximal end 2.33 of the modular body 2.15 preferably has an enlarged boss or platform 2.39 for fitting into the cavity 2.27 of the modular head 2.13. The platform 2.39 is adapted to be inserted through the side entrance opening 2.28 of said modular head 2.13 into the cavity 2.27 of the modular head 2.13.

The modular radial head sizer 2.11 preferably includes lock means 2.47 (see, in general, FIG. 37) for locking the modular head 2.13 and modular body 2.15 together after the platform 2.39 of the modular body 2.15 is inserted into the cavity 2.27 of the modular head 2.13 through the side entrance opening 2.28 of the modular head 2.13. The lock means 2.47 preferably includes ball-and-detent type means for locking the modular head 2.13 and modular body 2.15 together when the platform 2.39 of the modular body 2.15 is inserted into the cavity 2.27 of the modular head 2.13 through the side entrance opening 2.28 of the modular head 2.13 and rotated. The ball-and-detent type means may be any typical operation and construction now apparent to those skilled in the art such as a true ball-and-detent lock including a ball-and-spring means 2.51 in the opposite ends of the platform 2.39 as clearly shown in FIG. 13, and coacting detents or apertures 2.53 in the modular head 2.13 on opposite sides of the cavity 2.27 as clearly shown in FIG. 8 spaced 90° from the side entrance opening 2.28 so that the modular head 2.13 and modular body 2.15 will be locked together when the platform 2.39 of the modular body 2.15 is inserted into the cavity 2.27 of the modular head 2.13 through the side entrance opening 2.28 of the modular head 2.13 and rotated 90° as will now be apparent to those skilled in the art.

The proximal end or neck 2.55 of the stem 2.37 immediately adjacent the platform 2.39 of the modular body 2.15 preferably has at least two opposite flats 2.57 on the exterior thereof located parallel to the flat sides of the platform 2.39 for reasons which will hereinafter become apparent. The neck 2.55 may have three sets of opposite flats 2.57 to provide a hexagonal cross section as clearly shown in FIG. 15.

The modular head 2.13 and modular body 2.15 may be constructed in various manners and out of various materials as will now be apparent to those skilled in the art to substantially reproduce anatomical articular geometry. Thus, for example, the modular head 2.13 and modular body 2.15, except for the ball-and-spring means 2.51, can each be machined or otherwise constructed as a one-piece, integral unit out of a medical grade, physiologically acceptable material, in various sizes to fit a range of typical patients, etc. Preferably, the modular radial head sizer 2.11 includes a plurality of different size modular heads 2.13 and bodies 2.15 for allowing different size modular radial head sizers 2.11 to be assembled from individual heads 2.13 and bodies 2.15. Thus, for example, modular heads 2.13 may be provided to conform to the modular heads 13 of the modular radial head implants 11 with 5 different head diameters ranging between 20 and 28 millimeters in 2 millimeter increments, and with 3 different head heights ranging between 9 and 13 millimeters in 2 millimeter increments. Likewise, modular bodies 2.15 may be provided to conform to the modular bodies 15 of the modular radial head implants 11 with 5 different stem diameters ranging between 5.5 and 9.5 millimeters in 1 millimeter increments, and with 3 different stem lengths ranging between 20 and 24 millimeters in 2 millimeter increments. The various heads 2.13 and bodies 2.15 are preferably universally modular, so that all of the bodies 2.15 will work with all of the heads 2.13, and vice versa.

The system of the present invention includes modular radial head sizer insertion instrumentation for use in inserting the modular radial head sizer 2.11 into the elbow joint. The instrumentation including a modular sizer head insertion tool 3.13 and a modular sizer body holding tool 3.15 (see, in general, FIGS. 16–18).

The modular sizer head insertion tool 3.13 includes an elongated body 3.17 having a first end 3.19 and a second end 3.21. The first end 3.19 of the elongated body 3.17 of the modular sizer head insertion tool 3.13 includes a grip portion 3.23. The second end 3.21 of the elongated body 3.17 of the modular sizer head insertion tool 3.13 includes a threaded stud 3.25 for screwing into the threaded cavity 2.29 in the outer wall 2.23 of the modular head 2.13 of the modular radial head sizer 2.11.

The modular sizer body holding tool 3.15 includes an elongated body 3.27 having a first end 3.29 and a second end 3.31. The first end 3.29 of the elongated body 3.27 of the modular sizer body holding tool 3.15 includes a grip portion 3.33. The second end 3.31 of the elongated body 3.27 of the modular sizer body holding tool 3.15 has a mouth 3.35 with two opposite and parallel jaws 3.37 for engaging the flats 2.57 of the neck portion 2.55 of the stem 2.37 of the modular body 2.15 of the modular radial head sizer 2.11 to allow the modular sizer body holding tool 3.15 to hold the modular body 2.15 of the modular radial head sizer 2.11 against rotation. The elongated body 3.27 preferably has a double bend 3.39 between the first and second ends 3.29, 3.31 as clearly shown in FIG. 17 to provide enhanced finger clearance adjacent the grip portion 3.33 as will hereinafter become apparent.

The modular sizer head insertion tool 3.13 and modular sizer body holding tool 3.15 may be constructed in various manners and out of various materials as will now be apparent to those skilled in the art. Thus, for example, the modular sizer head insertion tool 3.13 and modular sizer body holding tool 3.15 can each be machined or otherwise constructed as a one-piece, integral unit out of a medical grade or the like in various sizes to fit the respective modular head 2.13 and modular body 2.15 of the modular radial head sizer 2.11.

The system of the present invention includes a modular radial head broach 4.11 (see, in general, FIGS. 19–21) for use in preparing the medullary canal MC of the proximal end P of the radius R to receive the proper size modular radial head implant 11. The modular radial head broach 4.11 includes an elongated body 4.13 having a first end 4.15 and a second end 4.17. The first end 4.15 of the elongated body 4.13 includes a grip portion 4.19, either formed as a part thereof or attached thereto, and especially formed to be hand-gripped. The second end 4.17 of the elongated body 4.13 includes a cutting head 4.21 for shaping and enlarging the proximal end of the medullary canal MC. The elongated body 4.13 is preferably bent adjacent the cutting head 4.21 as indicated by the arrow 4.23 in FIG. 20, and the cutting head 4.21 is relatively short (shorter than the corresponding implant stem) to allow easy joint access and facilitate introduction into the medullary canal MC. The cutting head 4.21 preferably has a blunt, rounded tip 4.25 to protect the capitellum cartilage and prevent soft tissue disruption upon introduction to the joint space. Gentle cutting teeth 4.27 are formed on the sides of the cutting head 4.21 from longitudinal flats cut on the circumference of the cutting head 4.21, spaced every 30°.

The modular radial head broach 4.11 may be constructed in various manners and out of various materials as will now be apparent to those skilled in the art. Thus, for example, the elongated body 4.13 and cutting head 4.21 can be machined or otherwise constructed as a one-piece, integral unit out of a stainless steel or the like, in various sizes to fit a range of typical patients, etc. The grip portion 4.19 may be machined or otherwise constructed as a separate unit out of Radel polymer or the like and press fitted or otherwise joined to the first end 4.15 of the elongated body 4.13. Preferably, the system of the present invention includes a series of modular radial head broaches 4.11 having different size cutting heads 4.21 for allowing the medullary canal MC to be prepared with different internal diameters to receive different size stems 37 of different size modular bodies 15, etc. Thus, for example, modular radial head broaches 4.11 may be provided to conform to the modular bodies 15 of the modular radial head implants 11 with 5 different stem diameters ranging between 5.5 and 9.5 millimeters in 1 millimeter increments.

The system of the present invention includes modular radial head radius crank planer 5.11 for use in preparing the proximal end P of the radius R to receive the modular radial head implant 11. The modular radial head radius crank planer 5.11 provides a "bit and brace" style hand-powered instrument to provide central axis loading with off-axis, bi-directional rotation to provide planing action for the resected end of the radius R. The modular radial head radius crank planer 5.11 includes an elongated shaft 5.13 having a first end 5.15 and a second end 5.17, a handle or knob 5.19 for mounting to the first end 5.15 of the shaft 5.13, a cutting head 5.21 for mounting to the second end 5.17 of the shaft 5.13, and a grip member 5.23 for mounting to the shaft 5.13 between the first and second ends 5.15, 5.17 thereof (see, in general, FIG. 22). The cutting head 5.21 has an elongated arm 5.25 terminating in a cutting or planer portion 5.27. The cutting or planer portion 5.27 is in the form of a flat disk with a plurality of cutting teeth 5.29 on one side and a center slot 5.31 for mating with the neck portion 2.55 of the stem 2.37 of the modular body 2.15 of a modular radial head sizer 2.11. As shown in FIG. 23, the direction of the cutting teeth 5.29 preferably changes 30° every 60°. The profile of the cutting teeth 5.29 is preferably created from 1/16 inch (0.15875 centimeter) diameter ball ended slots spaced 0.070 inch (0.1778 centimeter) along the face of the cutting or planer portion 5.27. The shaft 5.13 is off-set as indicated by the arrow 5.33 in FIG. 22 so that a longitudinal axis 5.35 passing through the handle or knob 5.19 will pass through the center of the cutting or planer portion 5.27 as clearly indicated in FIG. 22.

The modular radial head crank planer 5.11 may be constructed in various manners and out of various materials as will now be apparent to those skilled in the art. Thus, for example, the elongated shaft 5.13, handle 5.19 and cutting head 5.21 can be machined or otherwise constructed out of a stainless steel or the like, in various sizes to fit a range of typical patients, etc. The grip member 5.23 may be machined or otherwise constructed as a separate unit out of Radel polymer or the like and rotatably positioned on the shaft 5.13. The cutting head 5.21 is preferably modular for replacement due to wear, etc.

Figure 25:
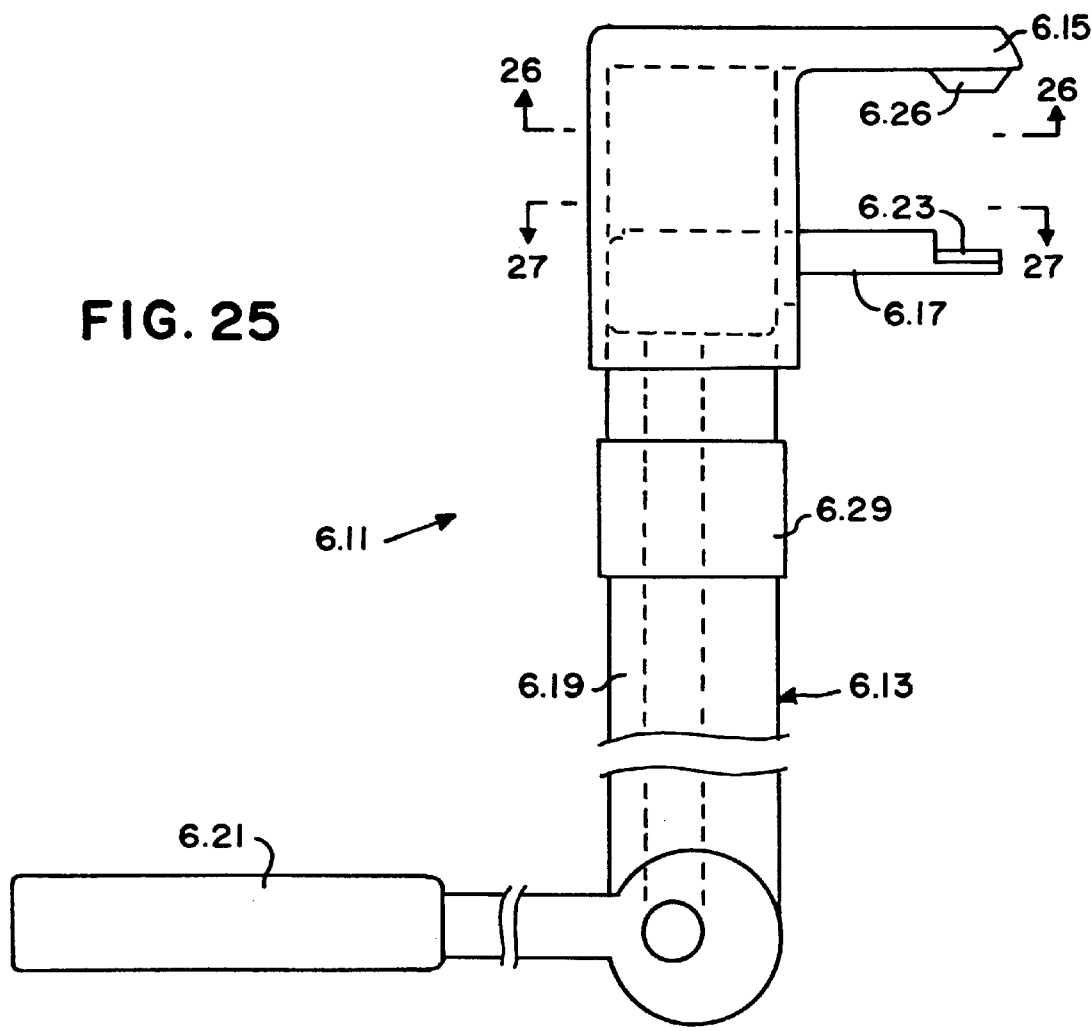
FIG. 25 is an elevational view of a preferred embodiment of a modular radial head locking instrument of the present invention, with portions thereof broken away for clarity.
Figure 26:
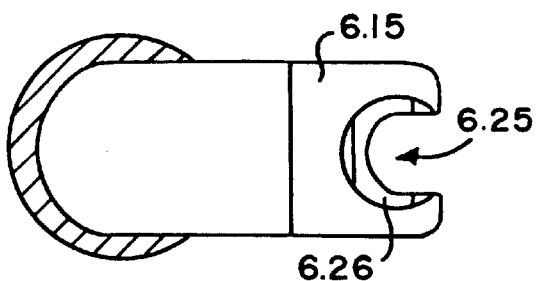
FIG. 26 is a sectional view substantially as taken on line 26—26 of FIG. 25.
Figure 27:
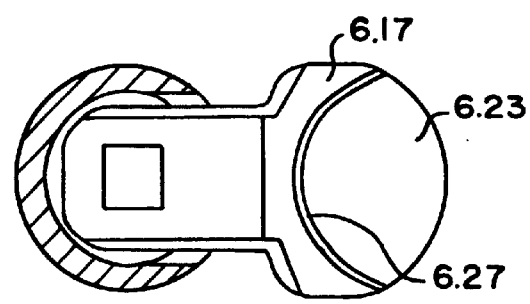
FIG. 27 is a sectional view substantially as taken on line 27—27 of FIG. 25.

The system of the present invention includes a modular radial head locking instrument 6.11 for use in locking a selected modular head 2.13 and a selected modular body 2.15 of the modular radial head implant 11. The modular radial head locking instrument 6.11 preferably includes an adapted femoral head extractor instrument 6.13 or the like such as the femoral head extractor instrument (No. 5014) manufactured and/or sold by Immedica, Inc. of 871 Mountain Avenue, Springfield, N.J. 07081. The locking instrument includes a first jaw 6.15, a second jaw 6.17, an elongated body 6.19, and a lever arm 6.21 or the like adapted to cause the first and second jaws 6.15, 6.17 to move toward one another (see, in general, FIG. 25). The first jaw 6.15 is adapted to engage the underside of the platform 39 of a modular body 15 of the modular radial head implant 11, and the second jaw 6.17 is adapted to engage the proximal end 17 of a modular head 13 of the modular radial head implant 11 as clearly shown in FIG. 40. A soft pad 6.23 manufactured out of plastic or the like is preferably provided on the jaw 6.17 to provide a soft interface with the proximal end 17 of the modular head 13 of the implant 11 to prevent implant damage. The first jaw 6.15 preferably has a distal end with a slot 6.25 therein for receiving a portion of the proximal end P of the radius R and/or the stem 37 of the modular body 15 of the modular implant 11. A portion of the first jaw 6.15 adjacent the slot 6.25 preferably forms a raised lip 6.26 for engaging the underside of the platform 39 of a modular body 15 of the modular radial head implant 11. The second jaw 6.17 preferably has a distal end with a modular centering means for receiving and positioning the modular head 15 of the modular implant 11. The modular centering means preferably consist of a curved wall 6.27 on the pad 6.23 to engage and position the proximal end 17 of the modular head 15 of the modular implant 11. The locking instrument 6.11 thus allows offset axial compression of the modular head 13 and modular body 15 of the implant 11. The instrument 6.13 may include the typical screw adjustment and force gauge mechanism 6.29.

The modular radial head locking instrument 6.11 may be constructed in various manners and out of various materials as will now be apparent to those skilled in the art. As hereinabove stated, the working mechanism of the locking instrument 6.11 preferably consist of an adapted Immedica femoral head extractor. The first and second jaws 6.15, 6.17 can be machined or otherwise constructed out of a stainless steel or the like. Several different size pads 6.23 (i.e., pads 6.23 with different size curved walls 6.27 to correspond to modular heads 15 having different diameters) may be machined or otherwise constructed as separate units out of Ultem polymer or the like corresponding to the different implant sizes, etc.

The surgical procedure or technique for using the modular radial head system of the present invention can vary as will now be apparent to those skilled in the art. The preferred surgical technique preferably includes the following steps:

1. Expose the radio-capitellar joint through a Kocher incision between the anconeus and extensor carpi ulnaris muscles. Carefully preserve the motor branch of the radial nerve at the radial neck N.
2. Using a surgical saw, the radial neck N is resected to the level of the fracture F or to the desired level of radial head resection. The annular and collateral ligaments are preserved where possible.
3. Using a starter broach or awl, an opening is created in the medullary canal MC. The appropriate modular radial head broach 4.11, based on pre-operative templating, is used to further shape the canal MC to receive the stem 2.37 of the modular body 2.13 of the modular radial head sizer 2.11 and the stem 37 of the modular body 15 of the modular radial head implant 11.
4. The stem 2.37 of the modular body 2.13 of the modular radial head sizer 2.11 is the inserted into the prepared medullary canal MC, and the cutting head 5.21 of the modular radial head crank planer 5.11 is slipped over the neck portion 2.55 of the stem 2.37, and rotated back and forth around the longitudinal axis 5.35 to create a plane surface on the resected end of the proximal end P of the radius R. The modular body 2.15 of the modular radial head sizer 2.11 will rotate with the cutting head 5.21 of the modular radial head crank planer 5.11. Axial force is applied to the handle 5.19 at the top of the crank planer 5.11 when the grip member 5.23 is moved in an arc about the longitudinal axis 5.35.
5. The appropriate modular head 2.13 of the modular radial head sizer 2.11, based on pre-operative templating, is screwed onto the threaded stud 3.25 of the modular sizer head insertion tool 3.13. The mouth 3.35 of the grip portion 3.33 of the modular sizer body holding tool 3.15 is placed onto the neck portion 2.55, or keyway, of the stem 2.37 of the modular body 2.15 of the modular radial head sizer 2.11 to hold the modular body 2.15 in place as the modular head 2.13 of the modular radial head sizer 2.11 is slipped onto the platform 2.39 of the modular body 2.15. The modular sizer body holding tool 3.15 keeps the modular body 2.15 from rotating with respect to the modular head 2.13. Once the modular head 2.13 has slipped over the platform 2.39 of the modular body 2.15, moving the modular sizer head insertion tool 3.13 with respect to the modular sizer body holding tool 3.15 causes the modular head 2.13 to rotate relative to the modular body 2.15. Once the modular head 2.13 has been rotated 90° (or a quarter-turn) relative to the modular body 2.15, the modular head 2.13 and modular body 2.15 will be locked together via the ball-and-detent means. Unscrew the modular sizer head insertion tool 3.13 and remove the modular sizer body holding tool 3.15, and perform trial reduction with the modular radial head sizer 2.11 in place. Good contact between the concavity 2.19 of the proximal end 2.17 of the modular head 2.13 and the capitellum C, and smooth rotation should be noted on passive flexion and rotation of the forearm.
6. If the trial reduction is not acceptable, applicable procedural stems 2–5, above, are repeated and trials chosen as appropriate.
7. Once sizing has been determined to be acceptable, the modular sizer head insertion tool 3.13 is reattached to the modular head 2.13, and the modular sizer body holding tool 3.15 is placed back into the neck portion 2.55, or keyway, of the stem sizer. The modular head 2.13 is unlocked from the modular body 2.14 by rotating the modular head 2.13 a quarter turn, or 90°, relative to the modular body 2.15 again, and the modular head 2.13 is removed from the joint space. The modular body 2.15 is then removed from the joint space and the joint thoroughly irrigated.
8. The appropriate size of modular body 15 is selected and placed into the radial canal MC. The appropriate size of modular head 13 is selected and prepared for implantation. Using finger control, the modular head 13 is placed into the joint space with the female taper of the cavity 27 of the modular head 13 over the male taper of the platform 39 of the modular body 15. At this point, the modular head 13 and modular body 15 are not locked together, but are in position to be locked together.
9. Based on head implant size, the appropriate assembly tool head insert 6.23 is placed onto the second jaw 6.17 of the modular radial head locking instrument 6.11. The lever arm 6.21 of the modular radial head locking instrument 6.11 is opened out away from the instrument body 6.19. Using the screw mechanism 6.29 on the instrument body 6.19, the jaws 6.15, 6.17 of the locking instrument 6.11 are adjusted to the approximate head height as denoted by graduations on the shaft, etc. The distal ends of the jaws 6.15, 6.17 are placed into the joint space so that the proximal end 17 of the modular head 13 of the implant 11 is resting on the plastic pad 6.23 of the jaw 6.17, and the platform 39 of the modular body 15 of the implant 11 is resting on the jaw 6.15 as clearly shown in FIG. 40. Final hand tightening of the assembly tool jaws 6.15, 6.17 is performed to eliminate any space between the jaws 6.15, 6.17 and the implant components. The lever arm 6.21 of the locking instrument 6.11 is brought toward the instrument body 6.19 until and audible click is heard. This click denotes that the 2000N-assembly force has been reached. Additionally, load can be visually verified on the force gauge 6.29 located on the instrument body 6.19. Continuing to apply load to the instrument 6.11 and implant 11 beyond the 2000N force may result in breakage of the instrument 6.11 or damage to the implant 11. If adequate joint space is available due to extensive fracture, etc., the implant 11 may alternatively be assembled in the same manner outside the body. The two implant components 13, 15 are placed into the jaws 6.15, 6.17 of the locking instrument 6.11, the jaws 6.15, 6.17 are tightened onto the implant components 13, 15, then the 2000N-assembly load is applied to the two components 13, 15 by forcing the lever arm 6.21 toward the assembly tool body 6.19.

10. The locking instrument 6.11 is removed from the joint space. The capsule, ligaments, and the anconeus and extensor carpi ulnaris muscles are sutured in layers with non-absorbable sutures, burying the knots.

As thus constructed and used, the preferred embodiment of the present invention provides:

(A) a modular radial head implant in which (1) the stem (body) and head components are modular; (2) the stem (body) and head components are assembled by a short 3° taper; (3) the components are highly polished and not fixed in bone (i.e., the implant is allowed to rotate, pivot and piston slightly); (4) the modular head reproduces the anatomical articular geometry; (5) the stem (body) components have drainage holes to allow for fluids trapped between the male and female tapers to drain out, thus improving the assembly; (6) the stem (body) and head components can be assembled intraoperatively (in vivo) or on back table; and (7) stem (body) and head components are universally modular—all stem (body) components work with all head components;

(B) a modular radial head sizer in which (1) the stem (body) and head components are modular; (2) the stem (body) and head components are assembled in a side loading manner via a slot and a groove, and rotated slightly to lock together; (3) the stem (body) components have two opposite flats under the platform or boss for coacting with a tool to keep the stem (body) from rotating as the head is rotated for locking; (4) the head component has a screw hole for receiving an insertion instrument to rotate the head component with respect to the stem (body) component to achieve locking; and (5) the head component has a slot that mates with the platform or boss of the stem (body) component, and a retaining groove that the platform (boss) spins in to capture the stem (body) component;

(C) modular radial head sizer insertion instrumentation consisting of a head sizer insertion tool and a stem sizer tool, and in which (1) the head tool has a threaded tip to rotate the head once it has been slipped onto the stem sizer; (2) the stem tool has a mouth with parallel flats which engage the parallel flats on the stem sizer to hold the stem sizer while the head sizer is rotated and locked onto the stem sizer; and (3) the stem sizer tool has a double bend to allow for finger space between the stem and head sizer handles to achieve the desired motion;

(D) a modular radial head broach, or series of broaches, in which (1) the broaches are left-hand cutting instruments used to shape the intermedullary canal of the proximal radius for the different size stem diameters of the modular radial head implants; (2) the broaches are much shorter than the implant stems and have bent shafts to allow easier joint access; (3) the ends of the broaches are blunt in order to prevent soft tissue disruption upon introduction to the joint space; (4) the cutting teeth are created from longitudinal flats cut on the circumference of the tool spaced every 30°; and (5) the cutting teeth cut when rotated counterclockwise and impact bone chips when rotated clockwise;

(E) a modular radial head radius crank planer consisting of a "Bit and brace" style hand-powered instrument to provide central axis loading with off-axis bi-directional rotation to provide planing action, in which (1) a portion of the crank planer is modular for replacement due to wear; (2) planer teeth are placed on one side of a flat disk, tooth direction changes 30° every 60° around the disk, and tooth profile is created from $\frac{1}{16}$ inch (0.15875 centimeter) diameter ball ended slots spaced 0.070 inch (0.1778 centimeter) along disk; and (3) the disk portion of the planer has a center slot for mating with the stem sizing instruments to facilitate centralization and perpendicularity of the planer on the radius; and (F) modular radial head locking components (head locker and stem locker) for fitting an adapted femoral head extractor in which: (1) the components allow offset axial compression of the modular radial head components; (2) modular Ultem pieces corresponding to the different stem sizes are interchangeable with the stem locking component; (3) the Ultem pieces provide a soft, elevated pad to compress the stem (body) components into the head components; (4) the head locking components incorporate a thin plastic pad as the implant/instrument interface to prevent implant damage; and (5) both components incorporate an I-beam shape to provide increased resistance to deflection under load.

Although the present invention has been described and illustrated with respect to preferred embodiments and preferred uses therefor, it is not to be so limited since modifications and changes can be made therein which are within the full intended scope of the invention.

What is claimed is:

1. A modular implant for replacing the head of the proximal end of a radius and for articulating with the capitellum of a humerus, said implant comprising:

(a) a modular head including a proximal end having a concavity therein for articulating with the capitellum of the humerus, and including a first lock member; and (b) a modular body including distal end for connecting to the radius, including a second lock member for coacting with said first lock member of said modular head to lock said modular head and said modular body together, and having a drainage passage allowing fluid trapped between said first and second lock members to drain out.

2. The implant of claim 1 in which said first lock member has a cavity with a female taper; and in which second lock member has a platform with a male taper for coacting with said female taper of said cavity of said first lock member of said modular head to lock said modular head and said modular body together.

3. The implant of claim 1 in which said modular head forms a circular disc; in which said modular head has a distal end; in which said modular head has an outer wall extending between said proximal and distal ends thereof; and in which said outer wall of said modular head curves outwardly between said proximal and distal ends thereof.

4. The implant of claim 1 in which said modular head reproduces the anatomical articular geometry of the proximal end of a radius.

* * * * *